United States Patent [19]

Gardner et al.

[11] 4,099,916
[45] Jul. 11, 1978

[54] INCENSE PRODUCT

[75] Inventors: Helen J. Gardner; Samuel M. Gardner, both of Wheaton, Ill.

[73] Assignee: Hindu Incense, Chicago, Ill.

[21] Appl. No.: 746,696

[22] Filed: Dec. 2, 1976

[51] Int. Cl.² .......................... A61L 9/00; A61L 9/01
[52] U.S. Cl. ..................................... 21/116; D23/78
[58] Field of Search ................................. 21/111–116, 21/74 R; 43/125–128, 144; 424/15, 40, 76; 431/288–297; D23/78; D73/1 R; 44/7.5

[56] References Cited

U.S. PATENT DOCUMENTS

| 108,109 | 10/1870 | Cone | 21/116 |
| D. 237,012 | 9/1975 | Steinhart | D73/1 R |
| D. 237,013 | 9/1975 | Steinhart | D73/1 R |
| D. 238,614 | 1/1976 | Steinhart | D73/1 R |
| 240,384 | 4/1881 | Carey | 21/111 |
| 498,025 | 5/1893 | Peirce | 21/116 |
| 1,110,796 | 9/1914 | Knorpp | 21/116 |
| 1,475,034 | 11/1923 | Slater | 21/116 |
| 1,866,931 | 7/1932 | Heffernan | 21/116 |
| 2,621,503 | 12/1952 | Schaefer | D73/1 R |
| 2,770,854 | 11/1956 | Miszeika | 21/116 |
| 3,380,797 | 4/1968 | Summers | D73/1 R |
| 3,706,523 | 12/1972 | Kumm | 431/288 |
| 3,917,441 | 11/1975 | Gray | 431/292 |
| 4,028,045 | 6/1977 | Reiher | 21/111 |

FOREIGN PATENT DOCUMENTS

| 4,310,109 | 4/1968 | Japan | 21/116 |

Primary Examiner—Morris O. Wolk
Assistant Examiner—Bradley Garris
Attorney, Agent, or Firm—Vogel, Dithmar, Stotland, Stratman & Levy

[57] ABSTRACT

The incense product includes a plurality of incense beads, each being a solid body with a hole. A rod passes through a selected number of the beads to provide a stand therefor.

9 Claims, 10 Drawing Figures

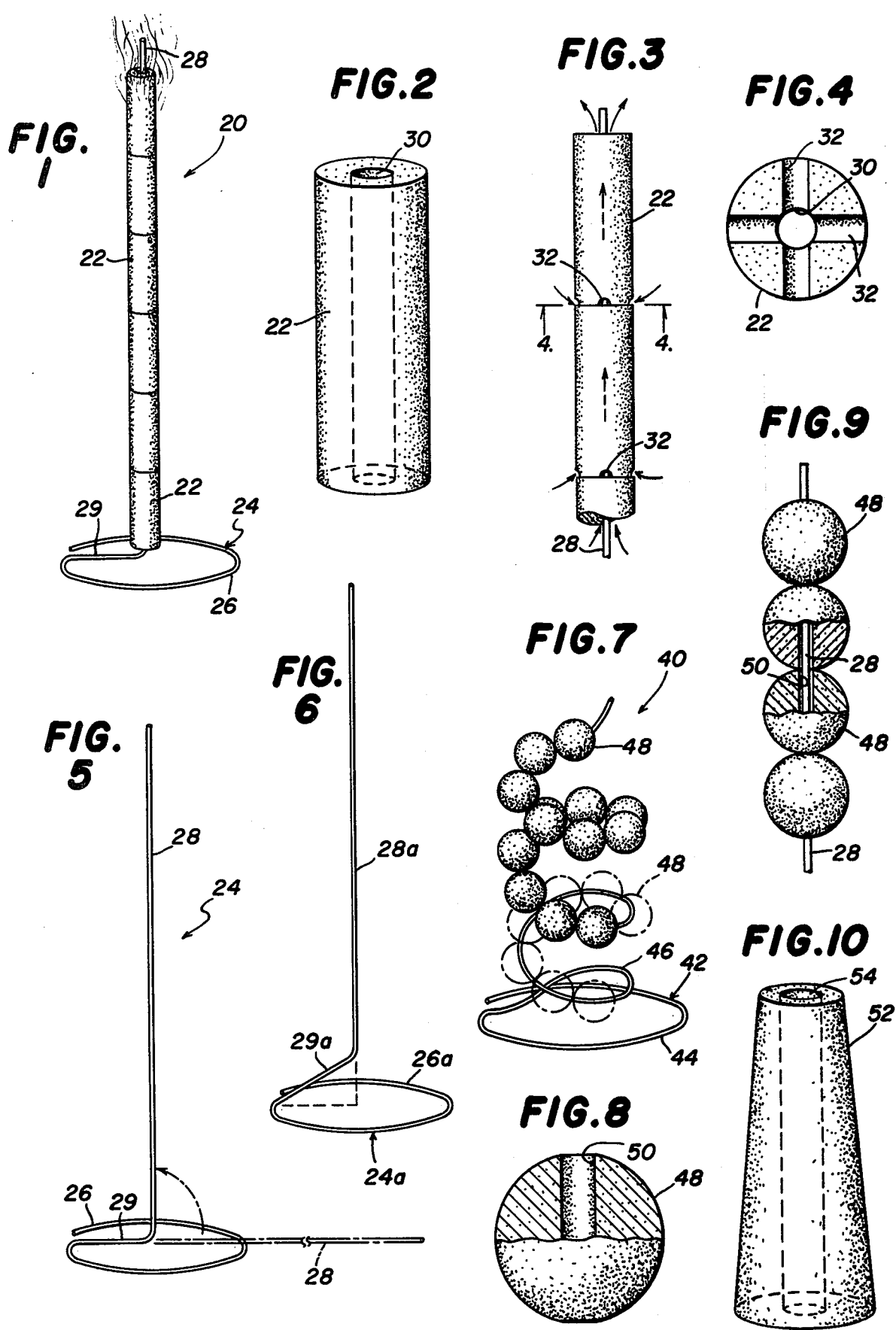

4,099,916

INCENSE PRODUCT

BACKGROUND OF THE INVENTION

There are basically two kinds of incense on the market today. One is a block of incense which may have a variety of bases such as charcoal or sandalwood, and a variety of shapes such as conical, frustoconical, pyramidal, rectangular, parallelepiped, and others. The incense block is lit and placed in an ashtray for example. As the incense burns, it emits a fragrance. A second basic kind of incense currently available comes in stick form. It has a long stick most of which is covered with a layer of incense material. The unlayered portion of the stick may be held or placed in the ground, for example, while the other end is lit. Again the burning incense emits a fragrance.

With either product, the burning time is fixed. However long it takes the block to burn out or however long it takes the incense stick to burn out is how long the incense will burn. Once lit, it is difficult to extinguish it without destroying its future usefulness. For example, the burning incense could be extinguished by dousing it with water. Obviously, however, it could not be used again.

In certain instances, it would be desirable to have incense which can continuously emit a fragrance for a long period of time, say an hour, without having to light additional pieces of incense. On other occasions, it might be desirable to have a very short burning time.

SUMMARY OF THE INVENTION

It is therefore an important object of the present invention to provide an incense product in which the burning time is adjustable.

Another object is to provide an incense product, having once selected a burning time, can readily be modified.

In summary, there is provided an incense product comprising a plurality of incense beads, each of the beads being a solid body with a hole therethrough, and a rod for passing through a selected number of beads to provide a stand therefor.

Further features of the invention pertain to the particular arrangement of the parts of the incense product whereby the above outlined additional operating features thereof are attained.

The invention both as to its organization and method of operation, together with further objects and advantages thereof, will best be understood by reference to the following specification taken in connection with the accompanying drawings.

BRIEF DESCRIPTION OF THE DRAWINGS

FIG. 1 is a perspective view of an incense product incorporating the features of the present invention, comprising a stand and a number of incense beads;

FIG. 2 is an enlarged perspective view of a cylindrical incense bead;

FIG. 3 is a view of a rod and several incense beads thereon, each incense bead having grooves in one end thereof;

FIG. 4 is a view on an enlarged scale taken along the line 4—4 of FIG. 3;

FIG. 5 is a view of the stand for the incense beads, showing the storage position in phantom;

FIG. 6 is a slightly modified incense stand;

FIG. 7 depicts an incense stand with a helical rod carrying incense beads spherical in shape;

FIG. 8 is a view partially in section of a spherical incense bead;

FIG. 9 is an elevational view of several spherical incense beads on a rod, a portion of two of the beads being shown in vertical section; and FIG. 10 is a perspective view of an incense bead which is frustoconical in shape.

DETAILED DESCRIPTION OF THE PREFERRED EMBODIMENTS

Turning now to the drawings and more particularly to FIG. 1 thereof, there is shown an incense product 20 which incorporates the features of the present invention. It comprises a plurality of cylindrical incense beads 22 supported by a stand 24, the stand 24 being formed from a single length of wire bent to form a base 26 and an upstanding rod 28 joined by a connecting link 29. The stand 24 may be formed of metal, extruded glass or nonflammable plastic.

As shown in FIG. 2, each incense bead is cylindrical, having a bore 30 extending therethrough along the longitudinal axis thereof. The composition of the incense beads 22 may be of any one of many. For example, it may be charcoal based, and impregnated with a selected perfume oil such as jasmine, strawberry or the like. When the incense bead 22 is lit, the perfume oil causes a corresponding fragrance to be discharged into the air. As an example, the incense bead 22 could have a diameter of one-quarter inch and a length of three-quarters of an inch.

Any number of the incense beads 22 may be threaded, one after another, onto the thin rod 28. The rod 28 has sufficient diameter and strength to be self-supporting. In the particular example of FIG. 1, six incense beads 22 have been threaded onto the rod 28. The incense product 20 may be placed in an ashtray for example and then a lighted match placed next to the top incense bead. After a few seconds, the top incense bead will become lit and will smolder, causing the fragrance to be emitted. The top bead 22 being in contact with the second bead, when the top bead has burned completely, the second bead will become lit and will begin burning. The beads 22 will thereby burn one after another until the bottom or last bead 22 is reached. The beads 22 may have ingredients to cause the ash to maintain its integrity, that is to say, retain the cylindrical shape even after they have burned. However, that is not essential to the present invention.

If instead of a burning time corresponding to six beads 22, one-third the burning time was sought, for example, then only two beads need be threaded onto the rod 28. The top of the second bead in such case is lit.

If having lit six beads, the user decides that he wants to extinguish the incense, he simply removes the burning incense, thereby preserving the balance for future use. For example, if only the top bead 22 is burning, then he could slip a card or a knife edge under such top bead and flip it off into the ashtray. The other five can be saved for future use.

Alternatively, instead of lighting the top bead, the bottom bead may be lit, whereby the bottom bead will burn upwardly until the second bead is lit, and so forth. Ultimately, the bead at the top will become lit to complete the burning of the column. When the burning is started from the bottom, it is slightly more difficult to interrupt the burning since all the beads that have been unlit including the one burning itself must be taken off the rod. Preferably, the unlit beads are first removed and saved for future use.

The burning may be commenced by threading all of the beads 22 onto the rod 28 and then lighting a selected one. Alternatively, the first bead 22 may be lit and then threaded onto the rod 28. The balance of the beads may then be threaded onto the rod. Also, additional beads 22 may be added. For example, if three of the six beads in FIG. 1 have been incinerated, three additional beads may be added, although this would likely cause burning toward both ends. Alternatively, if additional beads are added when the column begins burning at the bottom, the order of burning will remain bottom to top.

An additional feature of the invention is the improved burning characteristics caused by what may be termed a "chimney" effect. The burning incense draws air through the bores 30 in the beads 22. This aspect can be improved by providing grooves 32 (see FIGS. 3 and 4) at one end of each bead 22. The arrows in FIG. 3 show the path of air drawn into the bores 30 by way of these grooves 32.

The stand 24 is shown as such in FIG. 5. The solid line shows the use position, that is, the rod 28 extends substantially perpendicular to the plane of the base 26. The phantom line shows the position of the rod 28 in its storage position, whereupon the stand 24 is substantially flat for packaging. Instead of the rod 28 being integral with the base 26, it may be supplied as such, in which case it could be inserted into sand or into the ground, to cause it to stand upright. In such case, interruption of the burning beads 22 could be effectuated simply by withdrawing the rod, allowing the column to collapse.

FIG. 6 illustrates a slight modification in which corresponding parts bear the same reference numerals followed by the letter "a". In this form the connecting link 29a is not coplanar with the base 26a but instead projects upwardly. This produces a space between the bottom of the bottom bead 22 and the ashtray surface, to facilitate burning.

Another embodiment is depicted in FIG. 7. The incense product 40 includes a stand 42 having a base 44 which is generally round and a helical rod 46. In this case, spherical incense beads 48 each having a bore 50 extending diametrically therethrough, are threaded onto the rod 46. Again, in this embodiment, burning may be commenced either at the top or at the bottom. Alternatively, as shown in FIG. 9, the spherical incense beads 48 may be threaded onto a straight rod as such or a rod 28 which is part of the stand 24. FIG. 10 illustrates a bead 52 of frustoconical shape having a bore 54 extending along the longitudinal axis thereof. Such bead 52 may be threaded onto the rod 28 in the manner of FIG. 1.

What has been described therefore is an improved incense product which allows adjustability of the burning time. The beads may have a variety of shapes such as cylindrical, spherical, or frustoconical.

We claim:

1. An incense product comprising a plurality of incense beads, each of said incense beads being a solid body with a hole therethrough, and a stand including a rod and a base integrally formed of a single length of wire, said rod being adapted to pass through a selected number of said beads, the size of the hole of each bead being greater than the cross sectional size of said rod so that beads may be readily slipped onto said rod.

2. The incense product set forth in claim 1, wherein said body is substantially spherical and the hole therethrough is a bore extending diametrically through said body.

3. The incense product set forth in claim 1, wherein said body is frustoconical and said hole is a bore extending along the axis of said body.

4. The incense product set forth in claim 1, wherein said rod is substantially straight.

5. The incense product set forth in claim 1, wherein said rod is substantially helical.

6. The incense product set forth in claim 1, wherein said stand has a storage position in which said base and said rod lie substantially in a plane, and a use position wherein said rod is substantially perpendicular to the plane of said base, the composition of said stand being such that said stand is movable between said storage and use positions by bending said stand at the juncture between said rod and said base.

7. The incense product set forth in claim 1, wherein said base is substantially planar, and further comprising a link between said rod and said base and arranged to cause said rod to be outside the plane of said base.

8. The incense product of claim 1, wherein said body is cylindrical and the hole therethrough is a bore extending along the longitudinal axis of said body.

9. The incense product set forth in claim 8, wherein one end of said body is formed with radially extending grooves constituting a path for air to flow into said bore.

* * * * *